United States Patent [19]

Chevillon et al.

[11] Patent Number: 5,601,568
[45] Date of Patent: Feb. 11, 1997

[54] HANDLE FOR THE CONTROLLED RELATIVE SLIDING OF A SHEATH AND OF A STEM; APPARATUS COMPRISING SUCH A HANDLE AND METHOD FOR IMPLANTING A BLOOD FILTER USING A HANDLE

[75] Inventors: Gérard Chevillon, Montrouge; Guy Nadal, Poitiers, both of France

[73] Assignee: B. Braun Celsa (Societe Anonyme), Chasseneuil Du Poitou, France

[21] Appl. No.: 277,753

[22] Filed: Jul. 20, 1994

[30] Foreign Application Priority Data

Apr. 11, 1994 [FR] France .................... 94 04241

[51] Int. Cl.$^6$ ................................. A61F 11/00
[52] U.S. Cl. ............................ 606/108; 606/109
[58] Field of Search ................. 606/1, 107, 108, 606/113, 127, 138–148, 205–211; 604/208–211

[56] References Cited

U.S. PATENT DOCUMENTS

| | | | |
|---|---|---|---|
| 3,452,740 | 7/1969 | Muller | 606/108 |
| 3,754,555 | 8/1973 | Schmitt . | |
| 3,981,308 | 9/1976 | Schlein | 128/346 |
| 4,574,800 | 3/1986 | Peers-Trevarton . | |
| 4,777,948 | 10/1988 | Wright | 128/312 |
| 5,290,310 | 3/1994 | Makower | 606/108 |
| 5,409,478 | 4/1995 | Gerry | 606/108 |

FOREIGN PATENT DOCUMENTS

| | | |
|---|---|---|
| 0505686 | 9/1992 | European Pat. Off. . |
| 0518839 | 12/1992 | European Pat. Off. . |
| 0518838 | 12/1992 | European Pat. Off. . |
| 0536610 | 4/1993 | European Pat. Off. . |
| 0535370 | 4/1993 | European Pat. Off. . |
| 2606642 | 5/1988 | France . |
| 2652267 | 3/1991 | France . |
| 2657261 | 7/1991 | France . |
| WO91/19532 | 12/1991 | WIPO . |
| WO93/00130 | 1/1993 | WIPO . |

OTHER PUBLICATIONS

"Chronic Transvenous Pacemaker Lead Removal Using a Unique, Sequential Transveous System," Brodell et al. Amer. J. of Card. vol. 66, Oct. 1990, pp. 964–966.

Primary Examiner—Michael A. Brown
Attorney, Agent, or Firm—Rothwell, Figg, Ernst & Kurz, P.C.

[57] ABSTRACT

An operating handle for the relative sliding of a tubular sheath and a push-stem. The handle includes a hollow body with two opposite ends between which the stem extends axially. A carriage is detachably connected to the sheath and is movable within the body along an axial direction, and a control device is provided for controlling movement of the carriage. The control device includes a pivoting lever which causes the relative axial displacement of the sheath and stem. The invention finds particular application in the medical field for the implantation of medical devices such as blood filters.

10 Claims, 4 Drawing Sheets

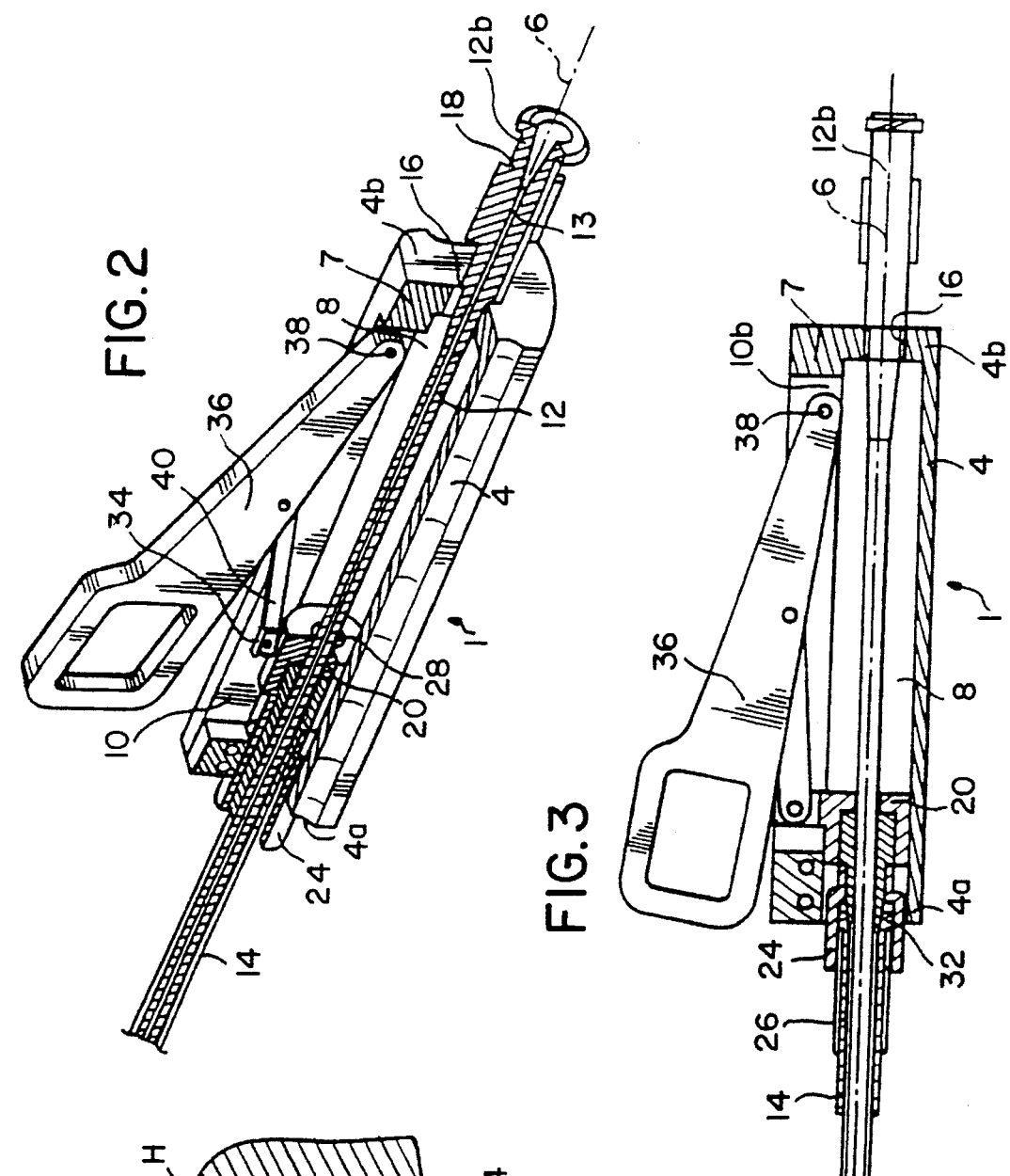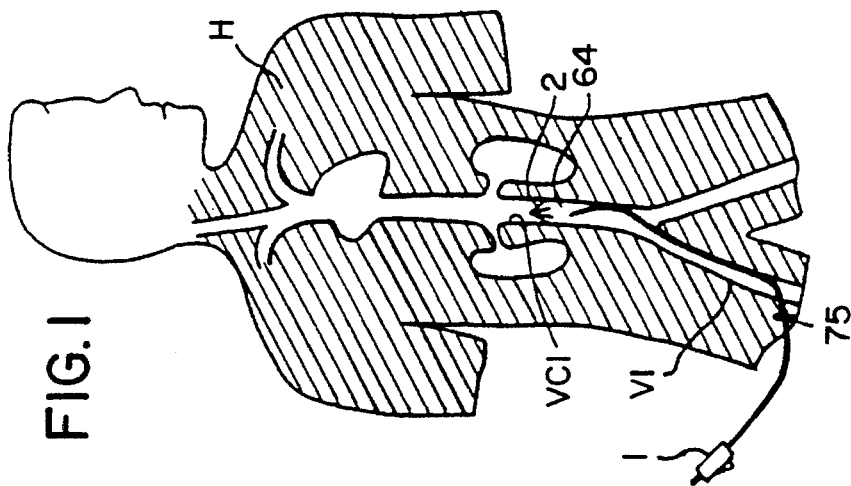

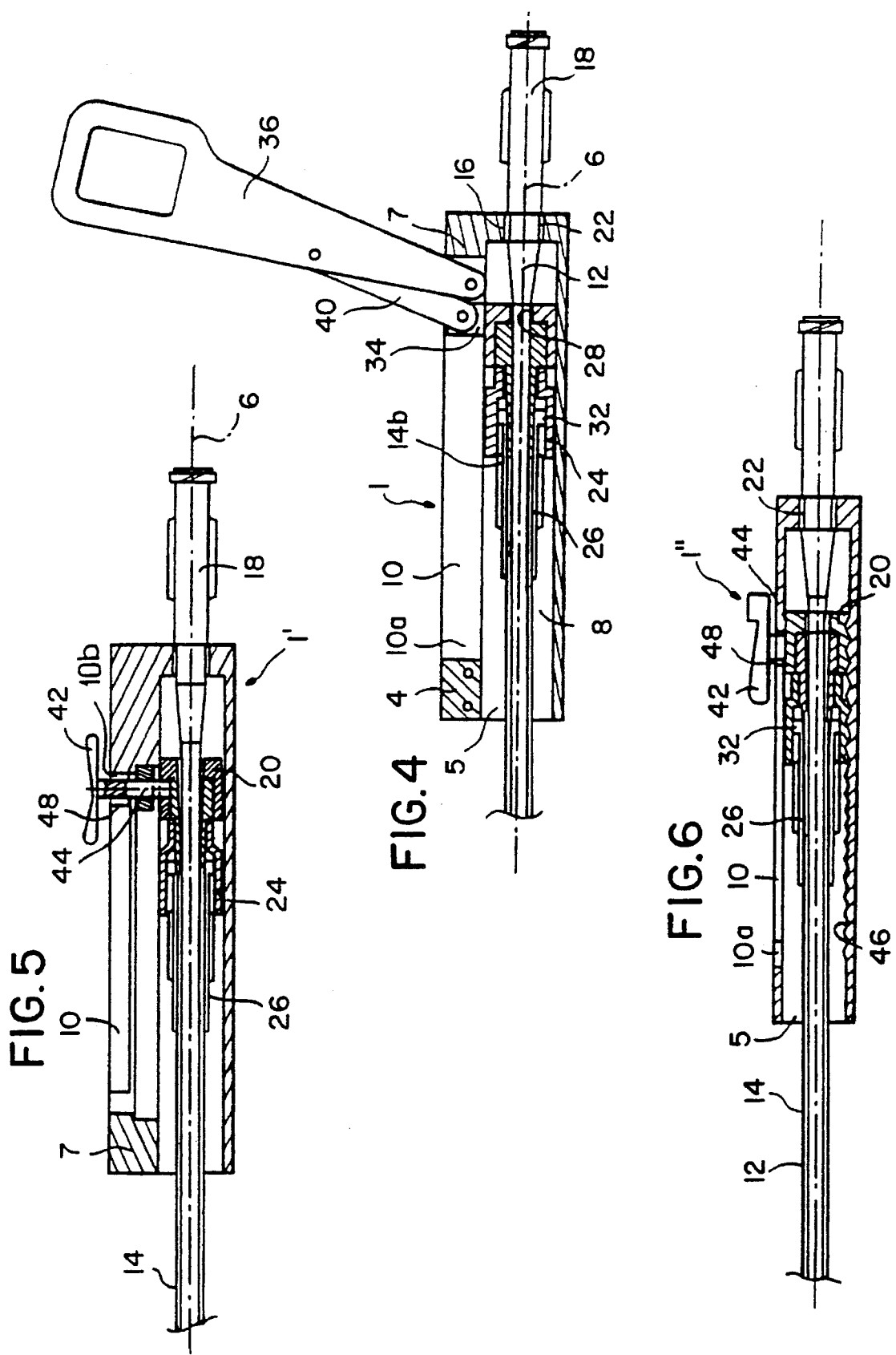

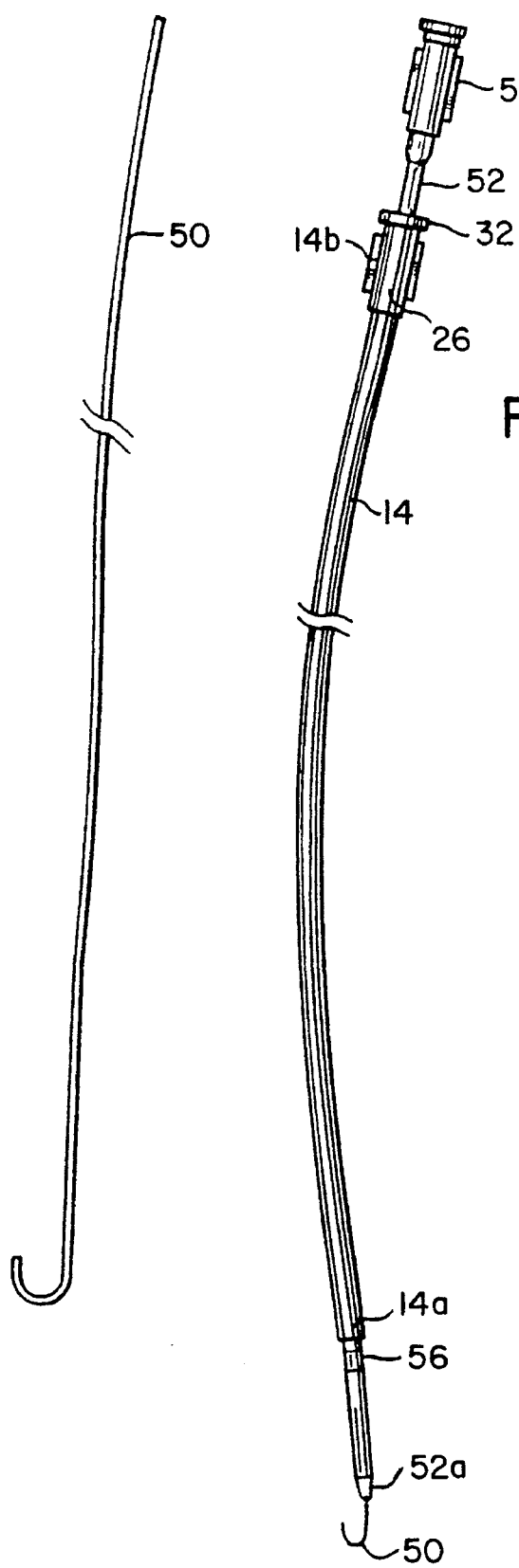
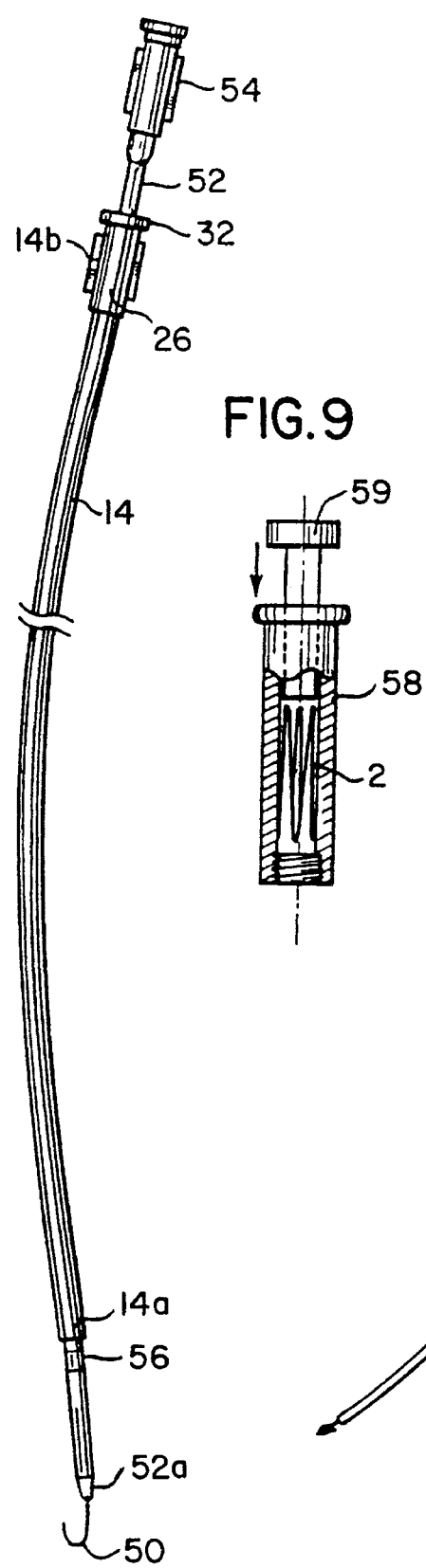
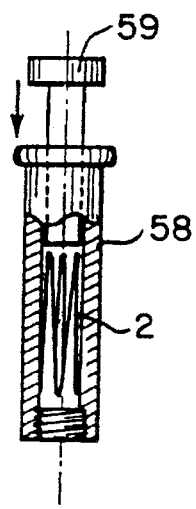
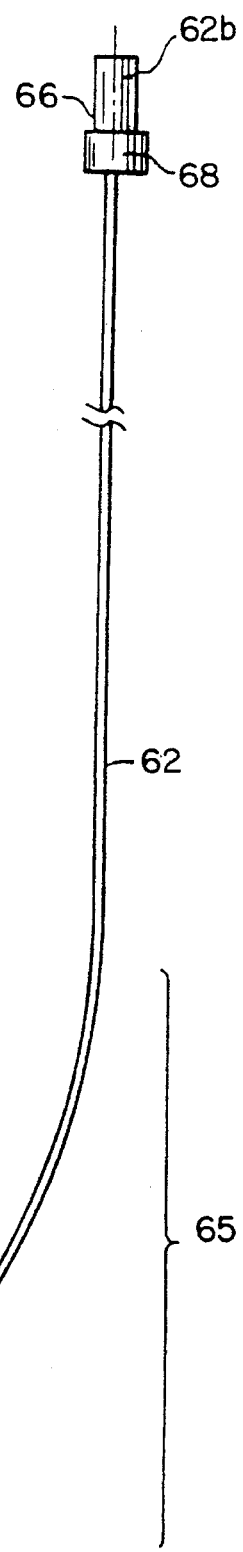

5,601,568

HANDLE FOR THE CONTROLLED RELATIVE SLIDING OF A SHEATH AND OF A STEM; APPARATUS COMPRISING SUCH A HANDLE AND METHOD FOR IMPLANTING A BLOOD FILTER USING A HANDLE

BACKGROUND OF THE INVENTION

The subject of the invention is an operating handle for the substantially coaxial relative sliding of a tubular sheath and of a stem suitable for being mounted in a sliding manner inside the sheath, and in particular in order to facilitate the implantation of a device in an implantation zone which is remotely accessible via this sheath and stem.

The invention is used more particularly in the medical field, for example, when it is necessary to implant an intravascular medical device (e.g., a blood filter, vessel dilator, and other prosthesis) in the body of a living human being or animal.

Assemblies for implanting intravascular medical devices are known and are described for example in patent application FR-A-2 657 261. They generally comprise a tubular sheath inserted into the body as far as the zone in which the device is to be implanted. The sheath is positioned by means of a guide wire and an introducer. These assemblies also comprise a push-stem which can slide in the sheath in order to move therein the device to be implanted. This device can thus be directed as far as the implantation zone where it is expelled from the sheath (by relative displacement of the sheath and the push-stem) and is implanted in the duct.

In practice, it is not always easy for the user to perform precisely and regularly the processes for the terminal positioning and optimum releasing of the device into the receiver duct.

SUMMARY OF THE INVENTION

In order to overcome these problems in particular, the invention proposes an operating handle for the substantially coaxial relative sliding of the sheathing and of the push-stem, this handle comprising:

a body which is axially open and is at least partially hollow; and connecting means between the body and, respectively, the sheath and push-stem for a substantially coaxial relative arrangement, these connecting means comprising a carriage which is mounted so as to slide axially in the body along a predetermined travel and is connected to the push-stem or to the sheath for their relative axial displacement under the action of means for controlling the sliding of the carriage, which means are accessible from the exterior of the body.

In this way, when the device is directed into the sheath and arrives substantially in the implantation zone, the user can maneuver it easily by means of the handle and move it very safely, in particular smoothly, until it is expelled from the sheath.

Preferably, and still with a concern for reliability, in particular in the medical field for releasing a blood filter or a vessel dilator or even some other vascular prosthesis, the sheath is firmly (yet detachably) secured to the carriage, whilst the push-stem is securely connected to the body (for example by screwing), rotatable indexing preferably being utilized.

In order to increase further the security of the handle and to be sure that there is no undesirable relative displacement of the sheath with respect to the push-stem, for example owing to the stresses which may be exerted thereon inside the patient's body, the control means advantageously comprise anti-return means for blocking the axial displacement of the carriage at the end of travel, a priori in the direction in which the device is expelled from the sheath.

According to a preferred embodiment, the control means comprise a lever which is movably mounted so as to rotate on the body and is functionally connected to the carriage, preferably via a connecting rod. Alternatively, the control means may make use of a slide or an indexed cursor which can move in translation along the axis of the body.

In order to permit easy access to the push-stem, it advantageously passes axially through the entire body, emerging at the exterior of the body at one end at least, the carriage then having an internal passage coaxial to the body so as to be mounted such that it slides about this stem.

Apart from the handle per se, the invention relates to medical equipment for specifically implanting a medical device in a human or animal internal duct, this equipment being characterised in that it comprises the above means, i.e. in particular the sheath, the push-stem and the above-mentioned operating handle.

In addition, in order to provide a solution to a consequent problem noted in correctly positioning the device in the duct, the invention proposes that the equipment can further be provided with:

a flexible centering cable, secured to its own handle and adapted so as to be disposed in at least part of the sheath in order to act there on the axial profile thereof by forcing its distal end, in an operating state, to be oriented towards the duct axis when the sheath is disposed there; and rotatable indexing means between the push-stem and the handle of the cable for holding them in a specific relative angular position in the operating state of the cable.

It is thus possible to position the distal ends of the sheath and the push-stem correctly and remotely and to ensure that the device is optimally inserted in this duct, more specifically during implantation by the femoral route.

For whatever purpose it may serve, it is noted that the term "distal end" of the sheath, for example, designates the end to be disposed as deeply as possible in the duct, "the proximal end" evidently being the opposite end which is to be located as close to the surface of the patient's skin as possible (within the scope of a medical application).

BRIEF DESCRIPTION OF THE DRAWINGS

The invention and its implementation will become clearer from the following description given with reference to the attached drawings, in which:

FIG. 1 is a schematic view in section showing implantation equipment according to the invention, used in this case for implanting a blood filter;

FIG. 2 shows the operating handle of the equipment connected to a sheath and to a stem in a schematic and partial view;

FIGS. 3 and 4 show the handle of FIG. 2, partially in cross-section;

FIG. 5 is a view partially in cross-section of a first variant of the handle of FIG. 2;

FIG. 6 is a view partially in cross-section of a second variant of the handle;

FIGS. 7, 8 and 9 show the principal elements conventionally used for positioning the filter shown in FIG. 1;

FIG. 11 shows a cable which can be used for centering the sheath relative to the axis of the implantation duct.

DETAILED DESCRIPTION OF THE DRAWINGS

Figure 10:
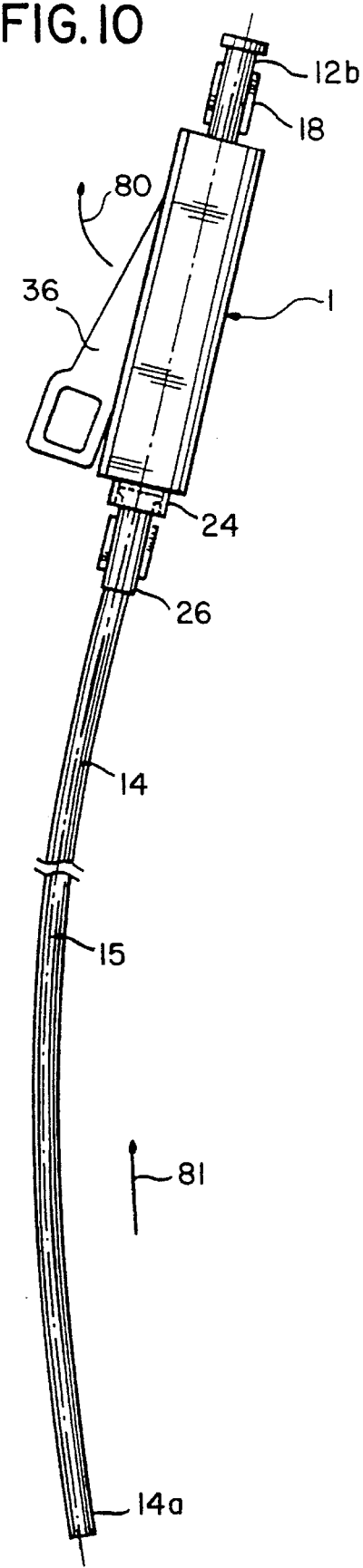
FIG. 10 shows again the equipment with the sheath, push-stem and handle of FIG. 2.

As one of the subjects of the invention is an operating handle for implanting a blood filter, in the following the invention will only be described in this respect, although it should be clear that other types of medical devices (such as "stents" or vessel dilators, for example), even if they are not vascular, may be concerned, and even non-medical applications can be envisaged.

FIG. 1 shows schematically an operating handle according to the invention, generally designated 1, which in this case is used for implanting a radially self-expanding metal blood filter 2, which is provided for limiting the risks of embolisms by restraining blood clots, in the inferior vena cava (VCI) of a patient H.

The handle 1, shown more precisely in FIGS. 2 to 4, comprises a body 4 which has an axis 6 which body is in this case rectilinear, and is made, for example, of plastics material, and here has an elongated shape which is open widely at 5 at one of its ends 4a.

This body 4, which is easy to hold, comprises an axial internal passage 8 emerging at the exterior at the end 4a. It also comprises an axial slot or window 10 provided in one of its walls 7 and communicating with the internal passage 8.

As illustrated, this handle 1 is connected firstly to a tubular sheath 14 and secondly to a push-rod 12 which can slide inside the sheath.

In this case, the push-stem 12 is secured to the body 4 at the location of an axial aperture 16 formed in the end wall 4b of this body opposite the end 4a.

This stem, which is fixed in translation, is advantageously also held immobile against rotation relative to the body by virtue of means for blocking against rotation and means for connecting fixedly in translation, for example by being screwed (threads 22), or possibly by being bonded in the aperture 16.

Thus, towards its proximal end 12b, the stem 12 passes axially through the passage 8 in the body via the opening 16 and even extends beyond it with an end piece 18 which is hollow and enlarged.

The sheath 14, with an axis extending therethrough, is connected at its proximal end 14b (FIG. 4) to the body 4 (the axes of body 4 and sheath 14 substantially coinciding at this location) via a carriage 20 mounted so as to be movable in axial translation in the passage 8.

In a preferred manner, this carriage 20 has a circular internal passage 28 of a diameter adapted so as to be mounted such that it can slide about the stem 12. In order to be secured to the sheath 14, the carriage in this case is associated with a coaxial threaded nut 24 of known type, for example a so-called "LUER" nut adapted to cooperate with the outer threads 32 of the proximal hollow end piece 26 of the sheath 14, the complete screwing together of the threads ensuring a connection which is fixed in translation for the two parts as well as advantageously blocking them against relative rotation.

Furthermore, the carriage 20 here has a projecting appendage 34 for its connection to control means. This appendage 34 is disposed in the slot 10 and prevents any rotational movement of the carriage relative to the body (the stem 12 and the sheath 14 thus being fixed against rotation relative to one another).

For its maneuver in translation, the carriage 20 is thus functionally connected to control means comprising, for example, an external lever 36 here mounted so as to be exclusively movable in rotation relative to the body 4 about an axis 38 perpendicular to the axis 6 (provided towards the "rear" or proximal end 10b of the slot). An articulated connection rod 40, which passes through the slot 10, connects the lever 36 to the carriage 20. The length of the connection rod 40 and the point at which it is secured on the lever determine the permitted travel of the carriage.

It will be noted that the lever can move between a first, front position (shown in FIG. 3), in which it extends along the body with the connection rod, and a second, rear position (shown in FIG. 4) in which it is straightened so as to be substantially perpendicular to the body. In this rear position, the connection rod is also straightened along the lever and thus blocks it in its rotational movement, preventing any forward movement and thus constituting an "anti-return" means.

FIG. 5 shows a first variant of the handle according to the invention, now bearing the reference numeral 1'. This handle 1' differs from the preceding one in that the control means now comprise a manual pusher or a slide 42 connected securely to the carriage 20 by means of a guide stem 44 which passes through the slot 10, thereby imposing an exclusively translational movement on the carriage. The travel of the carriage is here determined by the length of the slot 10, and an anti-return notch 48 in which the stem 44 can lodge is provided at the "rear" end 10b of the slot so as to block the carriage 20 at the end of its travel.

FIG. 6 shows a third version 1" of the handle of the invention. The means for controlling the handle 1" comprise a "notched system" whereas the control means of handle 1 are free of incremental means for a free displacement of the carriage. This notched system substantially consists of an outer slide 42 which is secured to the carriage 20 through a guide stem 44 and can be moved in translation along the axis 6. This system also comprises a notched axial surface 46, or the like, formed in this case by moulding in the inner wall of the body 4 which is opposite the slot 10, a cooperating notched surface of the carriage. As in the preceding variant, the control means comprise the anti-return notch 48 for blocking the slide.

Referring now to FIGS. 7 to 9, these show different known elements which can be used for positioning the medical device 2 (filter).

There can be seen a thin metal guide wire 50 and a guide piece or introducer 52 made of biocompatible plastics material, which enable the flexible plastic sheath 14 to be inserted in the inferior vena cava (CVI).

The introducer 52 with an enlarged head 54 is adapted so as to slide about the wire 50. This introducer further comprises a radio-opaque marking 56 towards its ogival distal end 52a.

The tubular sheath 14 has an internal diameter adapted such that the introducer, the push-stem and/or the filter (in the radially stressed position) can slide therein. Its length is adapted so as to leave the radio-opaque marking 56 visible when the introducer is completely inserted.

The push-stem 12, of which the length in practice is slightly greater than that of the sheath 14, is advantageously hollow (at 13) such that a centering cable 62 described below can slide therethrough or, possibly, such that a liquid can be injected into the zone 64 in which the device 2 is to be implanted.

FIG. 11 shows the centering cable 62 (of the type described in French application EN 93 11851 of 5th Oct. 1993) which is used more particularly for implantation via the femoral route, in which the sheath follows a curved, sinuous path in the patient's body H since the lefthand and righthand iliac veins form an angle with the inferior vena cava (FIG. 1). This cable consists, for example, of a pre-bent metal wire (at 65) which can be slid under stress inside the sheath (or even in the push-stem) so as to act on the profile of the axial line 15 of this sheath when it is implanted, forcing, by reaction, its distal end 14a to be directed towards the axis of the inferior vena cava. As shown, the cable terminates at its proximal end 62b in an enlarged handle 66 for holding the cable.

Figure 12:
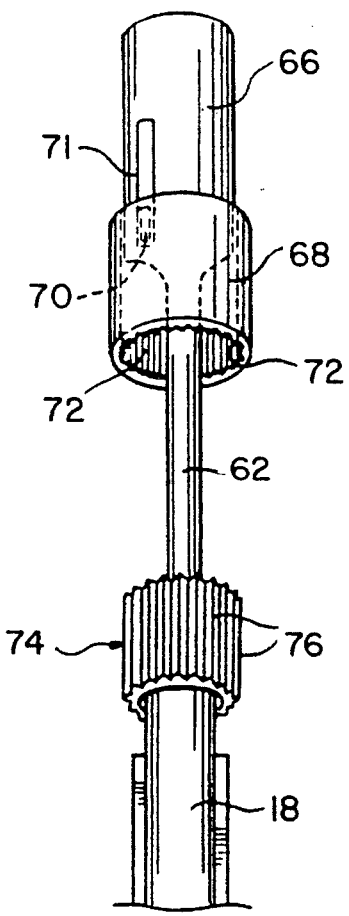
FIG. 12 shows the indexing means which the cable of FIG. 11 may comprise and the push-stem in an enlarged and partial view.

In accordance with the invention and as shown in FIG. 12, the system likewise comprises rotational indexing means functionally connected to the cable 62 and to the stem 12 respectively in order to hold them in a specific relative angular position when the sheath 14, the stem and the cable are correctly positioned in the duct (operating state of the cable), the cable then performing its role of a sheath "centering device."

Preferably, these indexing means comprise a part for locking in rotation, namely end piece 68, which is mounted so as to slide only in axial translation on the handle 66 of the cable by virtue of known guide means, such as a complementary longitudinal projection 70 and notch 71 provided one on the outer surface of the handle 66 and the other on the inner surface of the part 68. In this case, locking part 68 is axially hollow and has an internal diameter adapted so as to receive a complementary notched ring 74 which is securely connected (for example, screwed) to the free end of the end piece 18 of the stem 12. On the inner surface of its wall and the end piece 68 has longitudinal notches 72 complementing notches 76 formed on the outer surface of the ring 74.

According to a variant, it also is possible to provide for the indexing means to be functionally connected to the handle 1 and not to the end piece 18. Likewise, it is possible to invert the structure of these indexing means or even to dispose the sliding ring on the stem 12.

The use of the system according to the invention will now be described for the implantation of the filter 2, via the femoral route, in the inferior vena cava slightly above the kidneys, the patient H having had at least a local anaesthetic.

Firstly, the operator can either start by providing in the thigh (at 75) a percutaneous access route to the internal iliac vein VI or he can carry out the "denudation" of this vein.

He then introduces the guide wire 50 into the iliac vein as far as the inferior vena cava, slightly beyond the implantation zone 64.

The operator then enlarges the inlet aperture for the wire 50 and then fits the introducer 52, already introduced into the sheath 14, on the proximal end of this wire which emerges from the iliac vein.

He then lowers this assembly along the wire 50 until the radio-opaque marking 56 reaches the zone 64, whereupon the wire 50 and the introducer 52 can be withdrawn, the sheath 14 then being in position.

After screwing onto the end piece 26 a syringe body 58 (FIG. 9) containing the radially stressed filter 2, the operator can then slide the filter into the sheath 14 via the piston 59 of the syringe. The syringe body is then withdrawn from the proximal end of the sheath.

The operator then introduces the stem 12, associated with the handle 1, into the sheath and lowers it thereinto such that it pushes the filter to the distal end 14a of the sheath.

The end piece 26 of the sheath is then connected to the handle 1. Screwing this end piece into the nut 24 enables the sheath 14 to be placed in a specific fixed axial position relative to the stem 12, the respective lengths of the sheath and of the stem having been selected by the user such that, once they have been immobilized relative to one another, the filter is suitably disposed substantially just at the distal end 14a of the sheath.

If necessary, the cable 62 is then introduced into the stem 12, via the end piece 18, as far as an internal region of the sheath located upstream of its distal end part which then carries the filter. By adjusting the angular position of this cable relative to the stem and the sheath, or even the depth to which it is inserted, it is possible to alter the orientation of the end (14a) of the sheath.

The operator can control all these operations perfectly using known techniques such as radiography.

When the sheath has been positioned correctly, the cable is then blocked with respect to the stem by inserting the ring 74 into the part 68.

It then remains for a detachable safety strip (not shown), which hitherto locked the lever 36 along the handle, to be removed.

In order to expel the filter into the duct, the operator, holding the handle in one hand, then maneuvers the lever by moving it from its front position to its straightened, rear position (arrow 80). This causes the rearward displacement of the sheath 14 relative to the stem 12 which remains fixed (arrow 81, FIG. 10), with the expulsion of the filter which then expands naturally.

It only remains for the assembly consisting of the sheath, the stem and the cable to be removed and for the incision 75 to be closed in the conventional manner.

It will be appreciated that the invention is by no means restricted to the embodiments described. Thus, in relation to the variant in FIGS. 2 to 4, the lever 36 could have been connected directly to the carriage 20 (without the intermediary of the connection rod). The lever could then have been mounted at one of its ends so as to move both in translation and in rotation relative to the body 4 and, at an intermediate point between its opposite ends, mounted exclusively so as to rotate on the carriage. According to another variant, it would have been possible to maintain the sheath 14 fixed in translation and in rotation relative to the body 4, the sheath in this case being secured to the end 4a of this body, the push-stem 12 then being secured to the carriage so as to be movable in translation relative to the body. The slide 42 is then moved, for the expulsion of the filter, from the "rear" end 10b to the "front" end 10a of the slot, the anti-return notch 48 here being provided at the end 10a of the slot.

We claim:

1. A medical apparatus for the implantation of a radially expandable blood filter in an internal duct of a living body of a human being or animal, said apparatus comprising:

a tubular sheath adapted to receive internally, in a sliding manner, a blood filter in a radially folded state;

a push-stem slidably engaged within the sheath for relatively displacing the filter and the sheath;

an operating handle for substantially coaxial relative sliding of said sheath and said push-stem, said handle comprising:

a hollow body having an axis and including a front end and a rear end, said sheath and said push-stem being engaged with said hollow body, said push-stem extending axially between said front and rear ends of said hollow body;

a carriage slidably disposed in said hollow body so as to be axially movable therein along a predetermined path of travel;

a pivoting lever mounted on said hollow body for controlling the sliding of said carriage and inducing the relative axial displacement between said sheath and said push-stem so as to ensure that the blood filter emerges from said sheath and undergoes expansion;

wherein said push-stem includes a hollow tube which is fixedly secured to said hollow body and which emerges from said hollow body at the rear end thereof, and said sheath is detachably connected to said carriage; and wherein said pivoting lever is articulated on said hollow body adjacent to the rear end thereof and is movable from a first position in which the lever is in substantial parallel alignment with said hollow body to a second position in which the lever is disposed at an angle relative to said handle, wherein the blood filter is located in said sheath at said first position of the pivoting lever, and wherein the pivoting lever is moved to said second position to pull the sheath back relative to the push-stem so as to position the blood filter outside the sheath.

2. An apparatus according to claim 1, wherein the sheath has a proximal end and an opposite distal end, and further comprising a flexible centering cable adapted to slide inside said catheter of the push-stem to act on an axial profile of said sheath when said sheath is disposed in said duct, said cable being adapted to force said distal end of the sheath so as to be oriented towards an axis of the duct.

3. An apparatus according to claim 2, further comprising rotatable indexing means between said push-stem and said centering cable for holding the push-stem and centering cable in a specific relative angular position in an operating state of said cable.

4. In a medical implantation apparatus, an operating handle for the substantially coaxial relative sliding of a tubular sheath and a push-stem partially disposed inside the sheath, said handle comprising:

a hollow body having an axis and including an axially open front end for passing therethrough the sheath and the push-stem, and an axially disposed rear end;

a carriage disposed in said hollow body and being axially movable therein along a predetermined path of travel;

control means for controlling the sliding of said carriage within the hollow body, said control means comprising a pivoting lever mounted on said hollow body for inducing the relative axial displacement between the sheath and the push-stem, wherein said axially disposed rear end of the hollow body has means for being fixedly secured to said push-stem, and said carriage comprises connecting means for connecting said carriage to said sheath; and wherein said pivoting lever is articulated on said hollow body proximally to the rear end thereof and is movable from a first position in which the lever is in substantial parallel alignment with said handle to a second position in which the lever is disposed at an angle relative to said handle.

5. A handle according to claim 4, wherein said control means are free of structure which moves the carriage incrementally for permitting free displacement of said carriage relative to the hollow body.

6. A handle according to claim 4, further comprising means for blocking rotation of said sheath and push-stem with respect to each other and with respect to said hollow body.

7. A handle according to claim 4, wherein said control means comprise anti-return means for blocking the axial displacement of said carriage at the second position of said lever.

8. A handle according to claim 7, wherein said anti-return means comprise an articulated connection rod connected to said lever and to said carriage, said connection rod passing through an axial slot in said hollow body which communicates with the interior of the hollow body in which said carriage is located.

9. A handle according to claim 4, wherein said push-stem includes a catheter which emerges from the rear end of said hollow body to which it is fixedly secured.

10. A method for implanting a radially expandable vascular prosthesis in a vessel of a human being or animal, the method comprising steps of:

a) providing a medical apparatus comprising:

an operating handle for facilitating relative sliding of a tubular sheath and a push-stem, said handle comprising a movable carriage for displacing the sheath and a pivoting lever for controlling movement of the carriage;

wherein the vascular prosthesis is disposed in said sheath in a radially folded state before implantation in the vessel, said sheath having a proximal end and a distal end; and said push-stem is fixedly secured to the operating handle, said push-stem extending through the handle;

b) forming an access route in a body to an implantation zone for receiving the vascular prothesis;

c) introducing said sheath into the body through the access route and to said implantation zone while maintaining the proximal end of the sheath outside the body;

d) sliding the push-stem in a forward direction inside the sheath toward the distal end thereof;

e) detachably connecting the proximal end of the sheath to the carriage of the handle;

f) maintaining the handle and the push-stem in a fixed position relative to the body; and g) pivoting the lever of the handle from a first position in which the lever is in substantial parallel alignment with said handle to a second position in which the lever is disposed at an angle relative to said handle, said pivoting sliding the carriage rearwardly and displacing the sheath rearwardly to cause the vascular prothesis to emerge from the sheath and expand radially in said internal duct while said push-stem remains substantially stationary relative to said hollow body.

* * * * *